US00PP27643P3

(12) United States Plant Patent
Fazio et al.

(10) Patent No.: US PP27,643 P3
(45) Date of Patent: Feb. 7, 2017

(54) APPLE TREE ROOTSTOCK NAMED 'G.814'

(50) Latin Name: ***Malus domestica*×*Malus robusta* hybrid.**
Varietal Denomination: G.814

(71) Applicants: Cornell University, Ithaca, NY (US); The United States of America, as Represented by the Secretary of Agriculture, Washington, DC (US)

(72) Inventors: Gennaro Fazio, Geneva, NY (US); Terence Lee Robinson, Geneva, NY (US); Herbert Sanders Aldwinckle, Geneva, NY (US); James Cummins, Geneva, NY (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 120 days.

(21) Appl. No.: 14/120,454

(22) Filed: May 20, 2014

(65) Prior Publication Data
US 2015/0342101 P1 Nov. 26, 2015

(51) Int. Cl.
*A01H 5/08* (2006.01)

(52) U.S. Cl.
USPC ..... Plt./174

(58) Field of Classification Search
USPC ..... Plt./174
See application file for complete search history.

*Primary Examiner* — Keith Robinson
(74) *Attorney, Agent, or Firm* — Morrison & Foerster LLP

(57) ABSTRACT

The present invention relates to a new and distinct variety of apple tree named 'G.814'. 'G.814' is useful in that it can be propagated clonally and used as a rootstock or root system for apple trees as well as for interstems of apple trees. When used as a rootstock, 'G.814', is: dwarfing, induces scion precocity, is cold hardy, induces scion precocity, has a high yield efficiency, is tolerant to replant disease, and is resistant to: crown and root rot (*Phytophthora cactorum*), fire-blight (*Erwinia amylovora*), and powdery mildew. 'G.814' is susceptible to Apple Stem Grooving Virus (ASGV) and wooly apple aphid.

10 Drawing Sheets

STATEMENT REGARDING FEDERALLY SPONSORED RESEARCH OR DEVELOPMENT

This invention was made with United States government support under a United States Department of Agriculture-Agricultural Research Station Cooperative Research and Development Agreement, Sponsor's Contract Number 58-3K95-M-1031. The government has certain rights in the invention.

Genus and species: *Malus domestica*×*Malus robusta* hybrid.

Variety denomination: 'G.814'.

BACKGROUND OF THE INVENTION

I. Field and Utility Summary

The invention described herein is a new variety of apple tree, *Malus domestica*×*Malus robusta* hybrid, hereinafter referred to as 'G.814'. The new variety is useful as a dwarfing rootstock and is resistant to fire blight and crown rot. It is precocious and highly productive, and can be used as a rootstock and for interstems of apple trees.

II. Cultivation Summary

'G.814' originated from a planned cross in 1976 in Geneva, N.Y.

In the spring of 1976, pollen from a *Malus robusta* 'Robusta 5' apple tree (not patented) was applied to emasculated flowers of a *Malus domestica* 'Ottawa 3' apple tree (not patented) in Geneva, N.Y. In the fall of 1976, seeds resulting from this pollination were extracted from mature fruit derived from this cross. In the winter of 1976-77, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1977, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #814 was one of the survivors of this battery of inoculations from the same cross. All the surviving plants were transplanted to a field in Geneva, N.Y. in the fall of 1977. The surviving plants were then allowed to grow side shoots for propagation and evaluation. In 1980, 'G.814' was evaluated for rooting ability, lack of spine production, and low root brittleness in a layering bed (stool bed).

In 1984, three finished trees with 'G.814' rootstock were planted in a first test orchard in Geneva, N.Y. with *Malus domestica* cv. 'Northern Spy' (not patented) grafted onto this rootstock as the scion cultivar. This rootstock performed well (top 20% of many rootstocks tested) in these first test trials. In 1991, this rootstock was advanced to elite status based on field performance and four trees were planted with *Malus domestica* cv 'Empire' (not patented) for advanced evaluation. This planting was evaluated for twelve years resulting in the classification of 'G.814' in the dwarfing category similar to 'Malling 26' (not patented) apple rootstock and the cumulative productivity in the top 10% of the planting.

In 1994, an additional experimental orchard was planted in Geneva, N.Y. It featured several trees of 'G.814' as the rootstocks with scions 'Mutsu' (not patented), 'Haralson' (not patented), 'Royalty' (not patented), and 'Radiant' (not patented) to test the productivity with different scions. The tests resulted in acceptable performance with these scions.

In the spring of 2002, 'G.814' and other experimental rootstocks were planted as finished trees with 'Golden Delicious' (not patented) scion in Geneva, N.Y. In 2003 and 2004 the orchard was spray inoculated, while in bloom, with fire blight. All trees of 'G.814' survived, indicating good resistance of the rootstock in an orchard environment.

In February, 2002, several rootstock liners of 'G.814' were budded with Apple Stem Grooving Virus (ASGV) (*Capillovirus* spp.) infected wood and after the buds were healed the rootstocks were planted in a nursery in Geneva, N.Y. and monitored for survival and stunting. Measurements in August, 2002, showed that 50% of the plants had died and the surviving ones were stunted. These results indicated that this rootstock is susceptible to ASGV.

In summer, 2007, twenty rootstock liners were inoculated with two different strains of fire blight (ten liners per strain) in a greenhouse in Geneva, N.Y. As a result, the apple rootstock 'G.814' was classified as resistant to all of the strains tested. Furthermore, 'G.814' was observed to be susceptible to wooly apple aphid, resistant to powdery mildew, cold hardy, and tolerant of replant disease.

In the fall of 2005, the tree architecture of nursery trees was measured on 'G.814' and found that it promotes higher number of feathers and medium spreading habit on 'Gala' (U.S. Plant Pat. No. 03,637) scions.

III. Asexual Reproduction

Asexual reproduction of the 'G.814' apple rootstock has been achieved using the traditional method of clonally propagating apple rootstocks. In particular, the original seedling of the 'G.814' apple rootstock was planted in Geneva, N.Y., and allowed to develop into a "mother plant." The 'G.814' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.814' variety has been asexually reproduced in Geneva, N.Y., by root cuttings, by budding and grafting onto seedling and clonal rootstocks.

IV. Stability

Observations of trees from propagations in Geneva, N.Y. indicate that all clonally propagated trees have proven true to type and identical in all appearances to the original tree.

BRIEF SUMMARY OF THE INVENTION

The present invention relates to a new and distinct variety of apple tree named 'G.814'. 'G.814' is useful in that it can be propagated clonally and used as a rootstock or root system for apple trees as well as for interstems of apple trees.

When used as a rootstock, 'G.814' is: dwarfing, induces scion precocity, is cold hardy, induces scion precocity, has high yield efficiency, is tolerant to replant disease, and is resistant to: crown and root rot (*Phytophthora cactorum*), fire-blight (*Erwinia amylovora*), and powdery mildew (*Podosphaera leucotricha*). 'G.814' is susceptible to Apple Stem Grooving Virus (ASGV, *Capillovirus* spp.) and wooly apple aphid (*Eriosoma lanigerum*).

Characteristics of Parents, Comparators, and Distinguishing Features

Seed Parent—'Ottawa 3'

The seed parent *Malus domestica* 'Ottawa 3' is a dwarfing rootstock; trees grown on this rootstock are 30 to 35 percent the size of a standard self-rooted seedling tree. 'Ottawa 3' is known to induce good precocity to the scion (induces early reproductive development in the scion) and has high yield efficiency. 'Ottawa 3' plants produce no spines, are fairly well anchored, are a very cold hardy rootstock, and have resistance to crown and root rot caused by *Phytophthora cactorum*. However, 'Ottawa 3' is susceptible to the wooly apple aphid (*Eriosoma lanigerum*) and to fire blight (*Erwinia amylovora*). 'Ottawa 3' has been characterized as susceptible to ASGV.

Pollen Parent—'Robusta 5'

The pollen parent *Malus robusta* 'Robusta 5' is a non-dwarfing rootstock; trees on this rootstock are the same size as a standard self-rooted tree. 'Robusta 5' does not induce precocity to the scion and is not highly yield efficient. Juvenile plants of 'Robusta 5' produce many spines. 'Robusta 5' breaks buds very early in the spring and is winter-hardy. It is resistant to powdery mildew (*Podosphaera leucotricha*) and fire blight, and is immune to the wooly apple aphid. 'Robusta 5' on its own roots has a spreading architectural habit. Further, 'Robusta 5' has shown tolerance to the replant disease complex.

Comparison of 'G.814' with 'Ottawa 3'

'G.814' is distinguished from 'Ottawa 3' in that 'G.814' is resistant to fire blight, whereas 'Ottawa 3' is not resistant to fire blight.

'G.814' is similar to 'Ottawa 3' in that they share dwarfing properties, induce precocity to the scion, and are: yield efficient, cold-hardy, susceptible to ASGV, and resistant to crown and root rot caused by *Phytophthora cactorum.*

Comparison of 'G.814' with 'Robusta 5'

'G.814' is distinguished from 'Robusta 5' in that 'G.814' is: a dwarfing rootstock, induces scion precocity, and is highly yield efficient, while 'Robusta 5' is not a dwarfing rootstock, does not induce scion precocity, and is not highly yield efficient.

'G.814' is similar to 'Robusta 5', in that they share these properties: cold hardiness, resistance to fire blight, resistance to wooly apple aphid, resistance to powdery mildew, and tolerance of replant disease.

Comparison with 'Malling 26' ('M.26')

'G.814' is distinguished from 'M.26' in that 'G.814' is resistant to fire blight and tolerant of replant disease, whereas 'M.26' is not resistant to fire blight or tolerant of replant disease. 'G.814' exhibits finer, more branched root system than 'M.26' roots, resulting in higher exploration of the soil profile.

'G.814' is similar to 'M.26' in that they share these properties: dwarfing, scion precocity induction, and high yield efficiency.

Distinguishing Characteristics of 'G.814'

The 'G.814' apple tree is distinguished from 'Robusta 5', 'Ottawa 3', and 'M.26' in that 'G.814' has this combination of characteristics when used as a rootstock: dwarfing, induces scion precocity, high yield efficiency, fire-blight resistance, and replant disease tolerance.

BRIEF DESCRIPTION OF THE FIGURES

New apple tree rootstock 'G.814' is illustrated by the accompanying photographs. The ages of the trees depicted in the photographs are noted below. The colors shown are as true as can be reasonably obtained by conventional photographic procedures.

DETAILED BOTANICAL DESCRIPTION OF THE INVENTION

Figure 1:
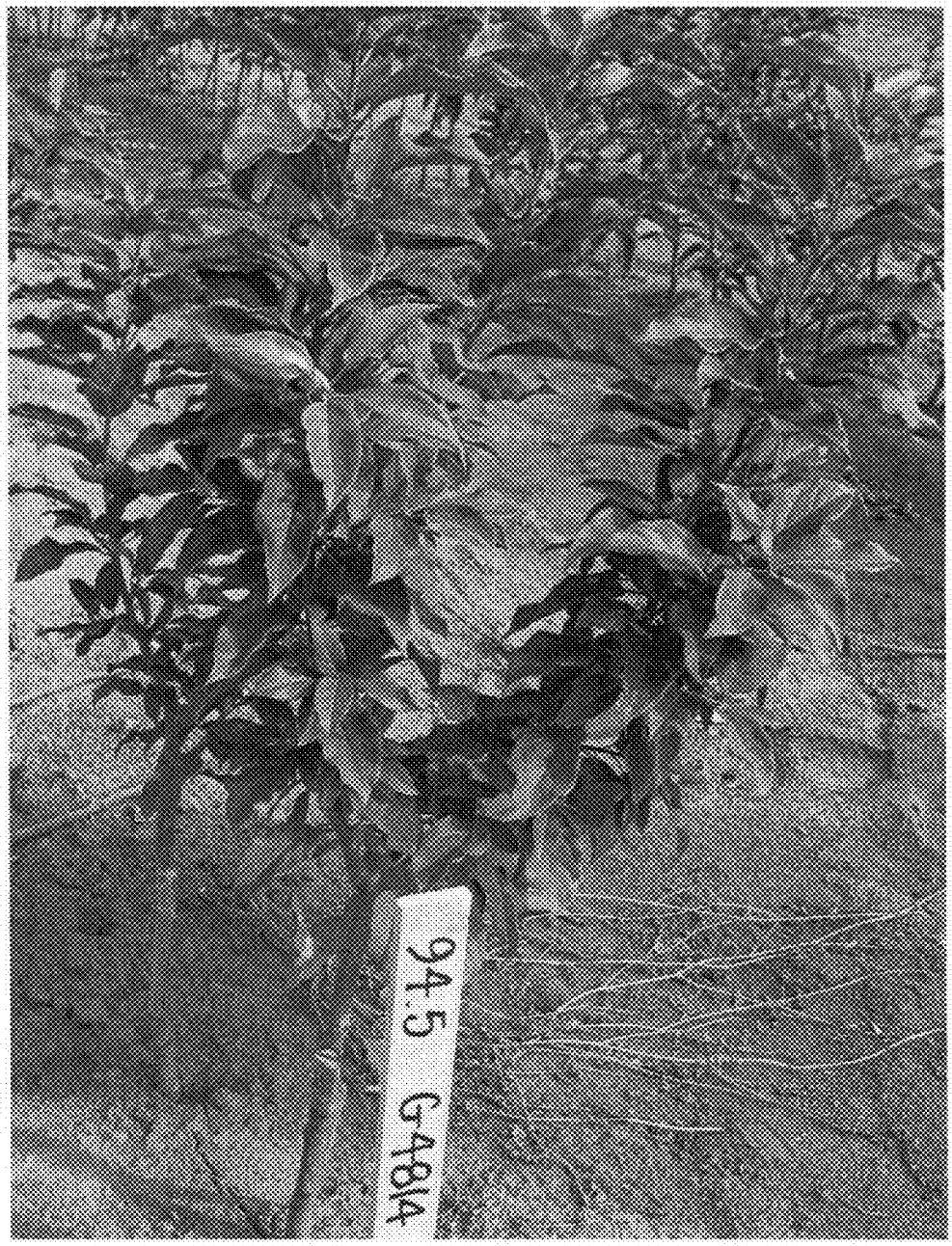
FIG. 1 is a photograph of 2-year-old 'G.814' liners in the nursery.
Figure 2:
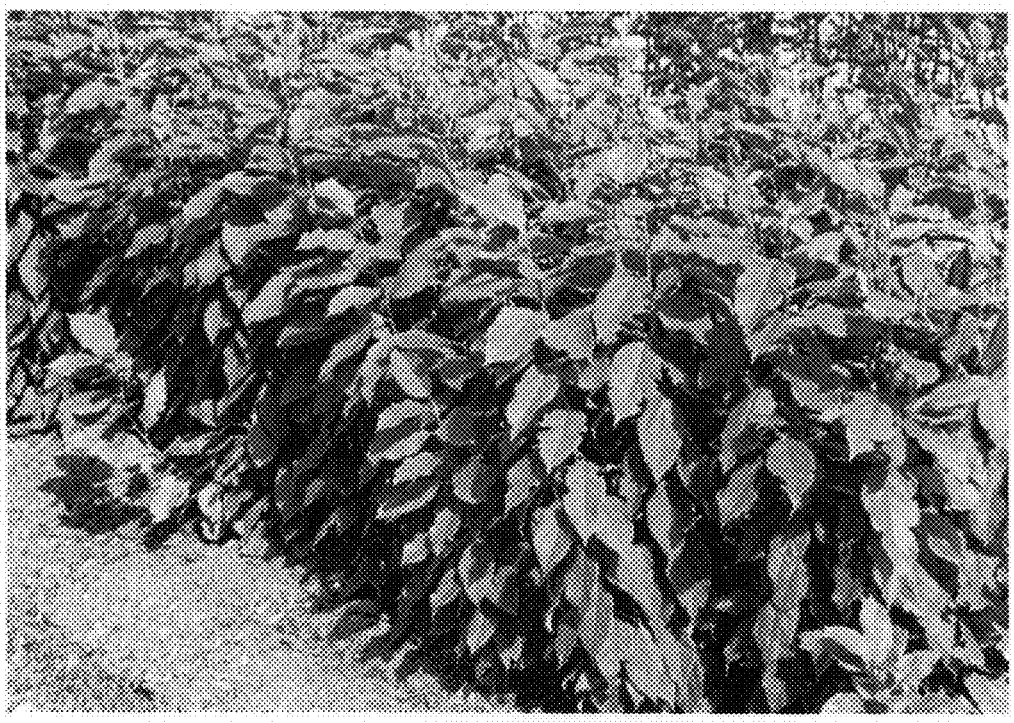
FIG. 2 is a photograph of live plants of 4-6 years in age in a propagation bed.
Figure 3:
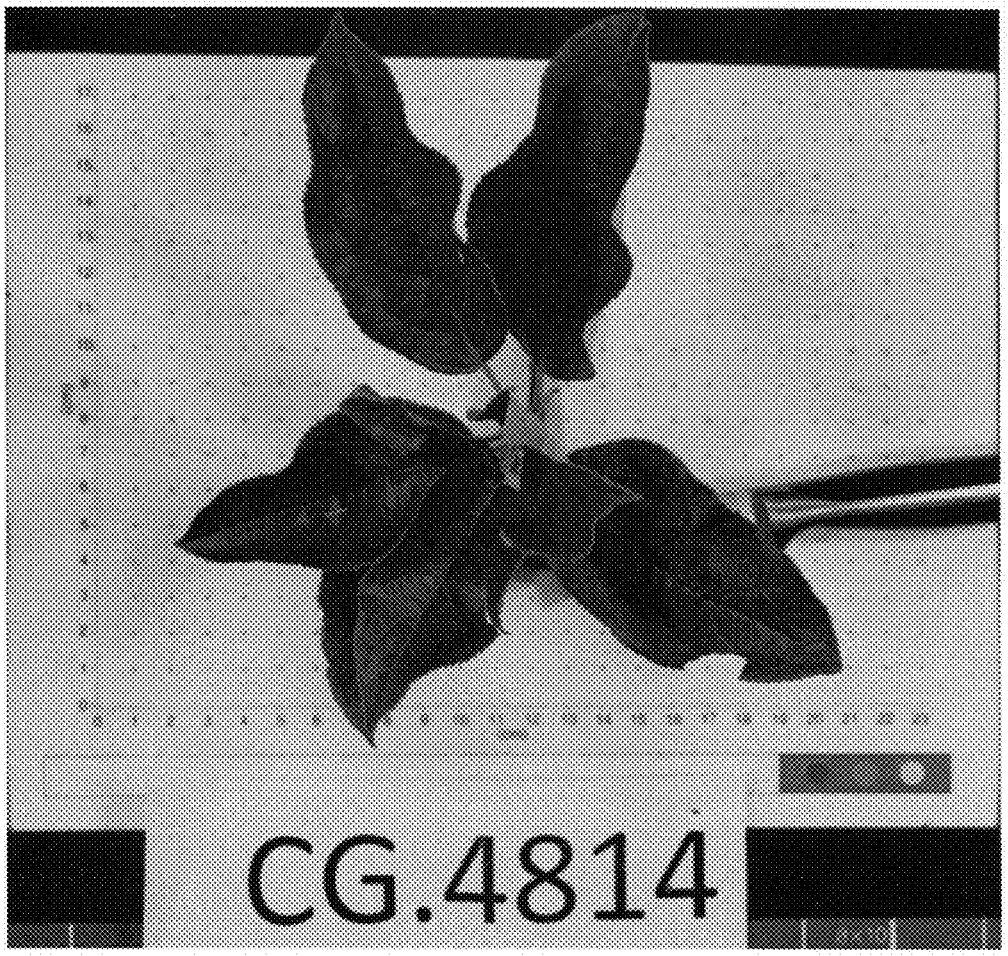
FIG. 3 is a photograph of leaves on the apex of a shoot of a 15-year-old plant.
Figure 4:
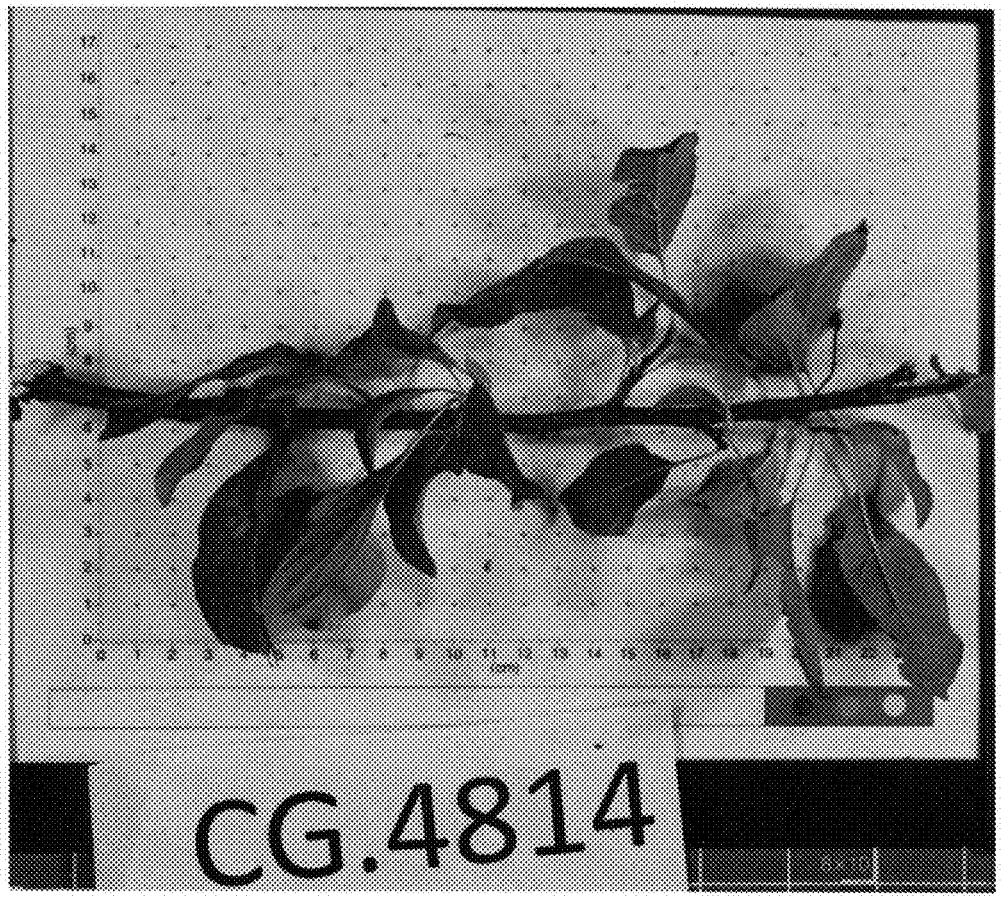
FIG. 4 is a photograph of a two-year-old shoot with leaf spurs and leaves.
Figure 5:
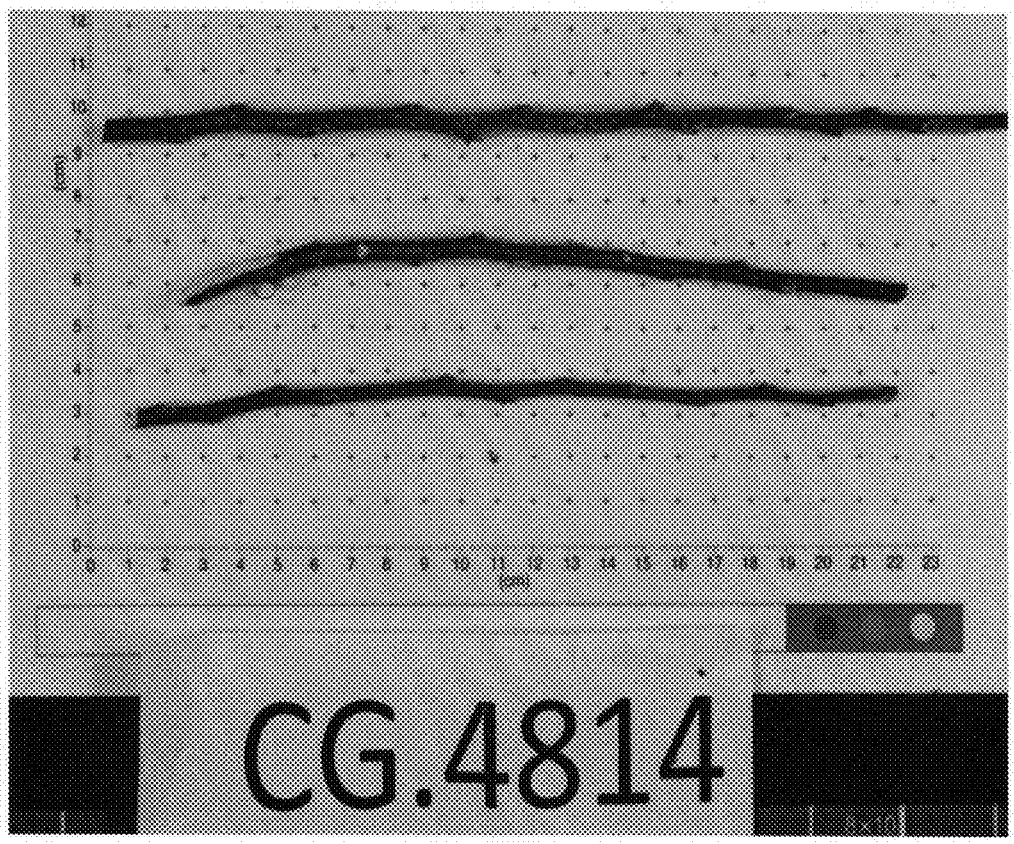
FIG. 5 is a photograph of bark and buds on a one-year shoot.
Figure 6:
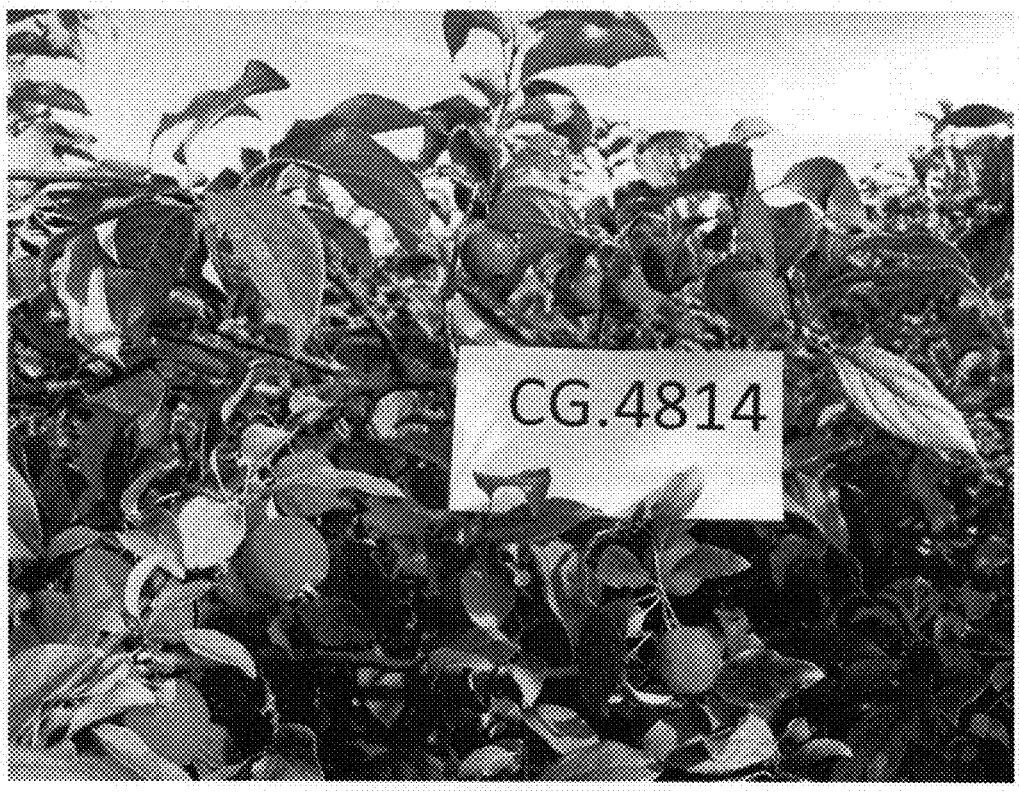
FIG. 6 is a photograph of fruit on a 15-year-old tree.
Figure 7:
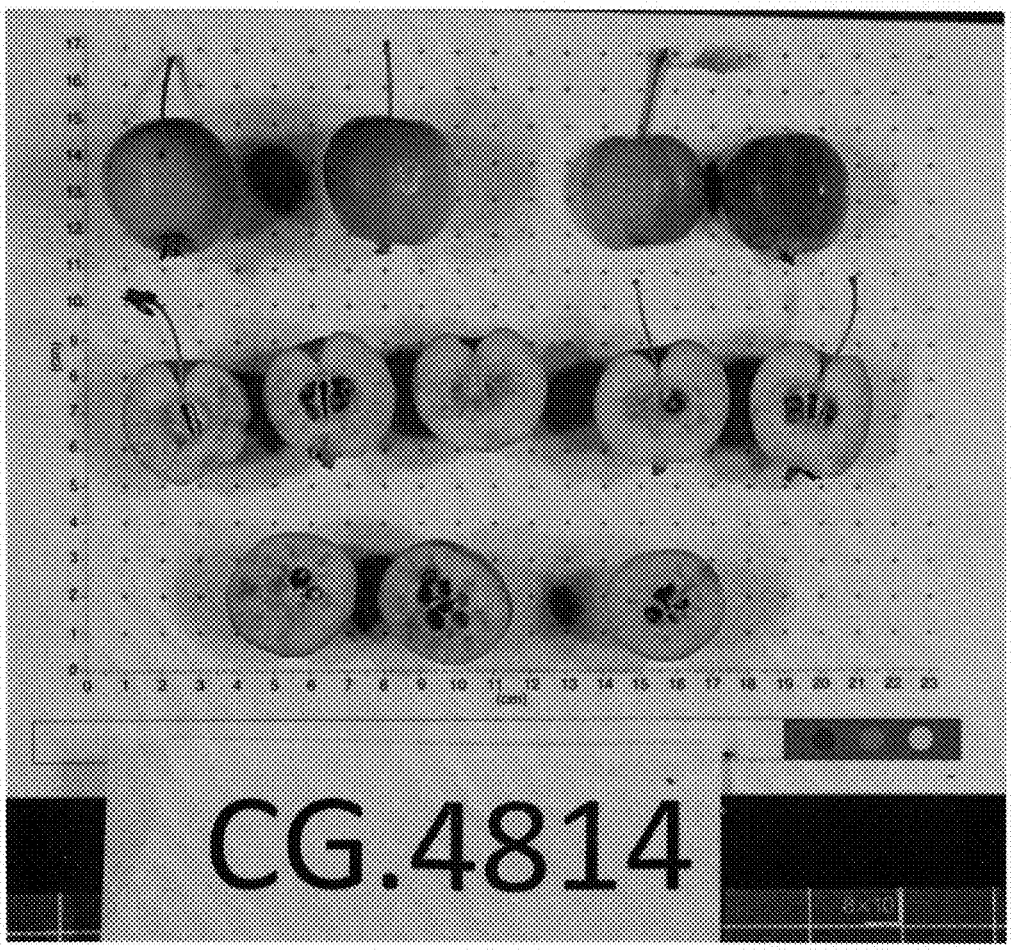
FIG. 7 is a photograph of fruit size, shape, and sections on a measuring board. Fruit is from a 15-year-old tree.
Figure 8:
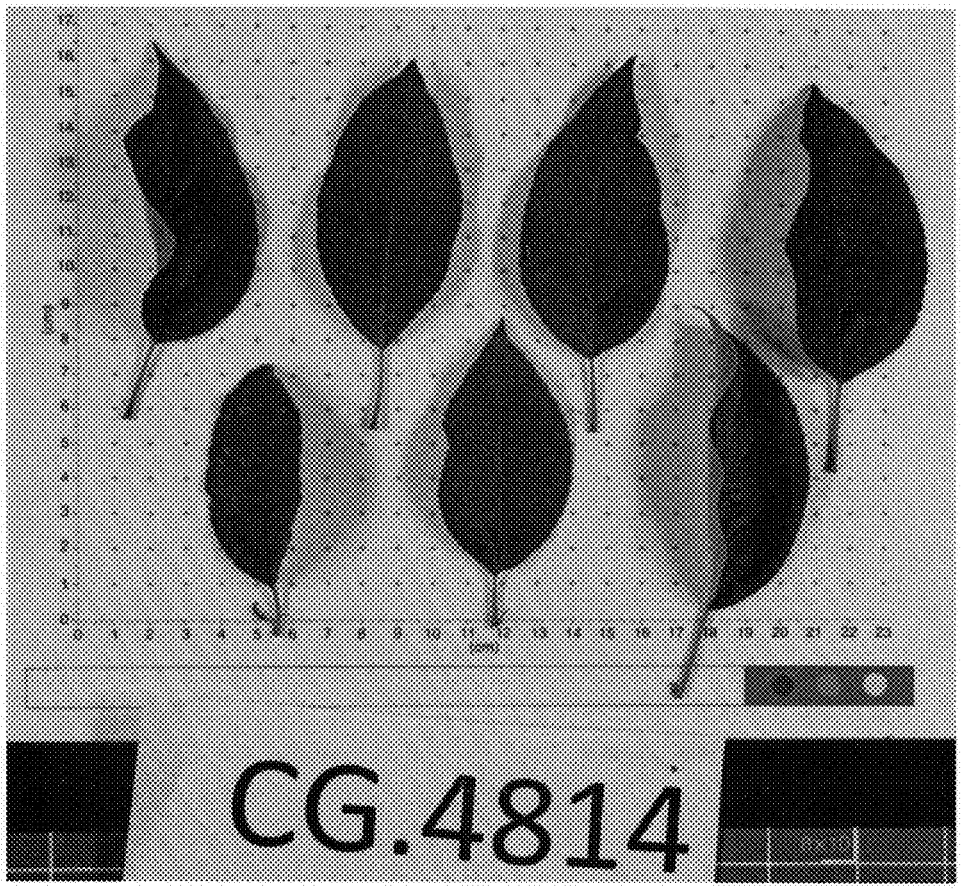
FIG. 8 is a photograph of mature leaf upper side, size, and shape on a measuring board. Leaves are from a 15-year-old tree.
Figure 9:
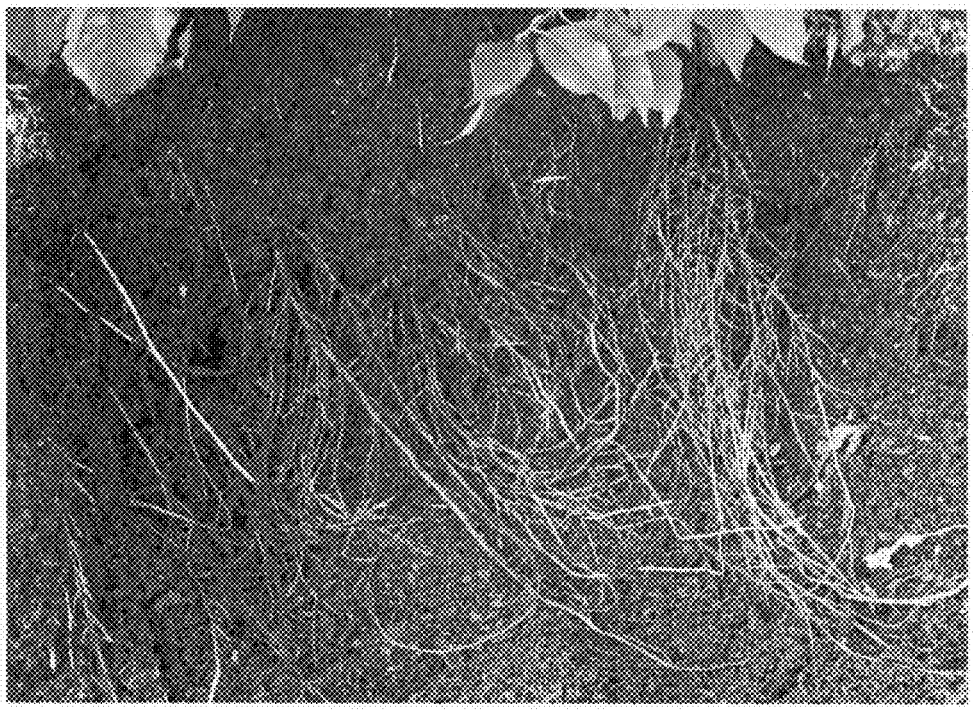
FIG. 9 is a photograph of fine or branched root production in a propagation bed of 4-6 years in age.
Figure 10:
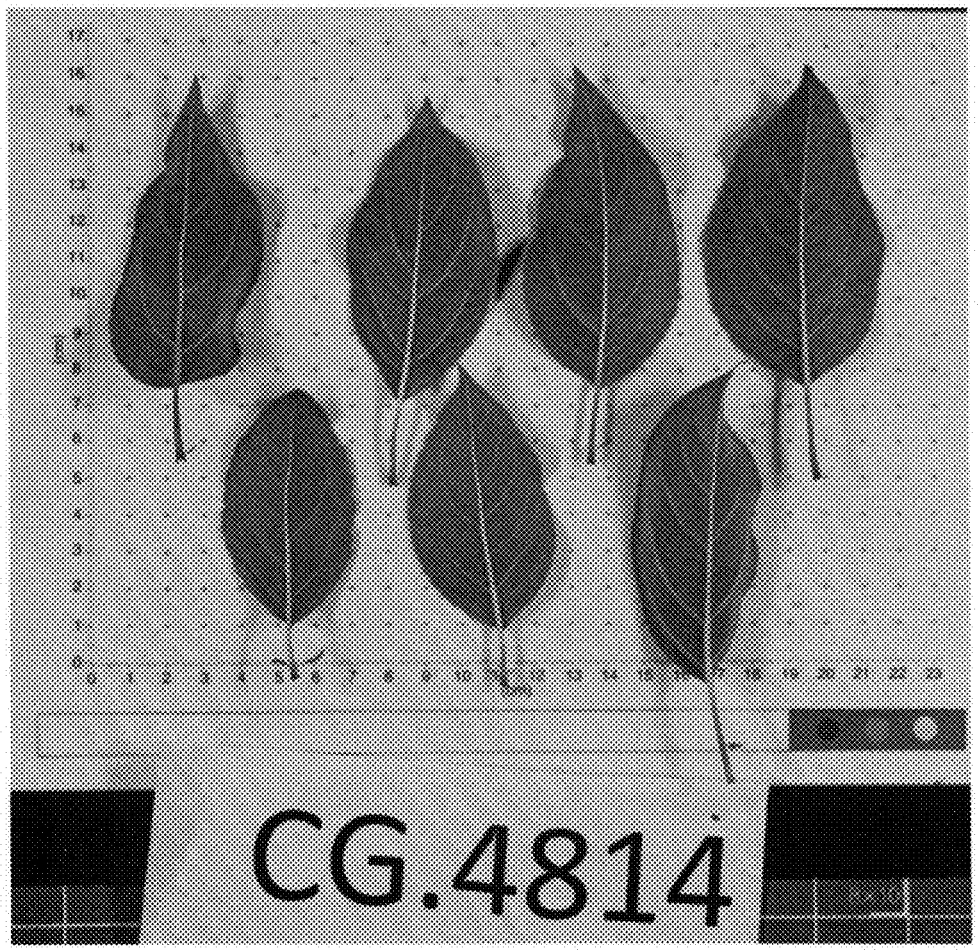
FIG. 10 is a photograph of a mature leaf lower side. Leaves are from a 15-year-old tree.

The following description of apple tree rootstock 'G.814' contains references to color names taken from The Royal Horticultural Society Colour Chart (R.H.S.), 2001 edition. Botanical descriptions follow the Manual of Cultivated Plants (Bailey, 1949).

Tree:

*Habit*.—Low vigor bush. A self-rooted tree of 'G.814' is a small shrub typically standing about 1.2-1.5 meters tall by about 1.5 meters wide when nine-years-old. There is no single dominant trunk. Instead there are few shoots arising from the crown. Some suckers (new shoots emerging from below ground) are produced. Liners planted in the nursery stop apical growth mid season. Root systems are very branched. Liners are straight with few spines. The apical bud in these plants is pubescent Greyed-Green (RHS 191D).

*Productivity*.—In an elite rootstock trial performed in Geneva, N.Y., the 'G.814' rootstock received the cultivar 'Empire' (*Malus domestica*) as the scion and was compared to the *Malus domestica* check rootstocks 'M.9' 'EMLA' (not patented) and 'M.26'. 'G.814' was shown to have statistically higher ($p \leq 0.05$) yield efficiency (kg yield/cm2 trunk cross sectional area) than all the check rootstocks.

*Precocity*.—Scion cultivars budded on 'G.814' exhibit the similar precocity as those budded on 'M.9'.

*Fertility* (*fecundity*).—The 'G.814' plant produces flowers and fruits regularly.

Dormant shoots (buds and bark):

*Color*.—Greyed-Red (RHS 178A) where exposed to full sunlight grading to Greyed-Orange (RHS 173B) with diminished light exposure.

*Texture*.—Very light pubescence which gradually disappears in older tissues. Size: 30-60 cm long; few spines.

*Axillary buds*.—Size: 2-3 mm long and 3 mm wide with little pubescence. Shape: Obtuse, sessile, somewhat appressed and flattened. Texture: Some pubescence.

*Bark on three-year-old shoots*.—Color: Greyed-Green (RHS 197A). Lenticels: Color: Greyed-Orange (RHS 163B). Size: 0.3-0.4 mm in diameter. Quantity: 1-2 lenticels per $cm^2$.

Leaves:

*Mature leaves*.—Leaf arrangement: Alternate. Shape: Simple, recurved, oblong-ovate. Size: Length: 85 mm. Width: 45 mm at the widest point. Laminae: Somewhat wavy. Apex: Acuminate. Base: Nearly symmetrical rounded. Margin: Acutely serrated, with about 5 serrations per cm. Upper surface: Color: Green (RHS 132B). Texture: Glabrous and translucent. Glossiness: Medium. Lower surface: Color: Greyed-Green (RHS 191B). Texture: Somewhat pubescent. Glossiness: Absent. Venation: Netted. Leaf poise: 355°-455° from the shoot, depending on shoot orientation. Stipules: Color: Green (RHS 132B). Length: 8 mm. Width: 2 mm. Petioles: Diameter: 2 mm. Color: Gradation of Green (RHS 140A) to Greyed-Red (RHS 179A) depending on low or high exposure to light. Texture: Smooth. Length: 1.7 cm on average.

Flowers:

*Habit*.—Flowers borne on spurs, shoot terminals, and from lateral buds on growth from previous season.

*Flower diameter*.—40 mm.

*Fragrance*.—None.

*Buds*.—Location: Located on spurs and terminals; are mixed, typically producing a truss of 5 to 6 flowers and one bourse shoot. Number: 5-6 flowers on bourse shoot. 2-4 in mid shoot. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2-4 flowers; and more distal buds are usually vegetative.

*Petals*.—Arrangement: Intermediate. Texture: Top: Venated. Bottom: Venated.

*Pedicel*.—Length: 28 mm. Diameter: 1.5 mm. Color: Yellow-Green (RHS 143A).

*Size*.—Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs*.—Pollen: Amount: medium. Color: Yellow-Orange (RHS 14C). Pistils: Number: 5. Length: 6 mm. Color: Yellow-white (RHS 145B). Stigma: Shape: Double kidney. Color: Yellow-White (RHS 158C). Ovary size: 5 mm in height and 5 mm in width. Ovary color (external): Red (RHS 46B). Stamens: Length: 4 mm. Color: White (RHS 155D). Another color: Yellow-Brown (RHS 167D). Anther: Length: 1.5 mm. Filament height: 8 mm. Shape:

Indented kidney. Color: Yellow-Orange (RHS 14C) with middle Yellow-Orange (RHS 22A).

Fruit:

*Mature fruit*.—Size: Height: 30-35 mm. Diameter: 30-35 mm. Shape: Round Obloid. Color: Partial Red-skin (RHS 45A) with Yellow-Orange (RHS 23B) blush undertones depending on the exposure to the sun. Sepals: Sometimes persisting on a variable protruding calyx. Flesh: Taste: Astringent (not meant for consumption). Color: Yellow-Orange (RHS 21C) with Red (RHS 42B) bleed through from the skin in mature fruits. Seed: Texture: Glossy. Color: Greyed-Red (RHS 178A), translucent. Shape: Tear drop shape. Size: Length: 50-60 mm. Diameter: 25-35 mm at the widest point. Number: Generally 5-7 seed per fruit.

Disease resistance: As described above, the 'G.814' rootstock of the present invention exhibits resistance to fire blight. The percent-lesion measured after inoculation of potted liners in the greenhouse using four different strains of *E. amylovora* was negligible for all strains tested in Geneva, N.Y. The 'G.814' rootstock, having survived the inoculation with crown and root rot, is also considered resistant to crown and root rots caused by *Phytophthora cactorum*. 'G.814' is susceptible to ASGV and wooly apple aphid.

We claim:

1. A new and distinct variety of apple tree named 'G.814' as herein described and illustrated.

* * * * *